United States Patent [19]
Rosen

[11] Patent Number: 5,859,066
[45] Date of Patent: Jan. 12, 1999

[54] METHOD FOR THE TREATMENT OF ITCHING

[75] Inventor: Robert T. Rosen, Pottersville, N.J.

[73] Assignee: Rutgers, The State University of New Jersey, New Brunswick, N.J.

[21] Appl. No.: 827,726

[22] Filed: Apr. 8, 1997

Related U.S. Application Data

[60] Provisional application No. 60/015,039, Apr. 8, 1996.

[51] Int. Cl.$^6$ ................................................ H61K 31/12
[52] U.S. Cl. ........................... 514/682; 514/23; 514/75; 514/643
[58] Field of Search ............................................. 514/682

[56] References Cited

U.S. PATENT DOCUMENTS

| | | | |
|---|---|---|---|
| 3,920,808 | 11/1975 | Fusaro | 424/59 |
| 3,974,281 | 8/1976 | Gadekar | 424/263 |
| 4,002,737 | 1/1977 | Borris | 424/94 |
| 4,112,067 | 9/1978 | Tomalia et al. | 424/78 |
| 4,137,301 | 1/1979 | Willer et al. | 424/45 |
| 4,141,966 | 2/1979 | Willer et al. | 424/45 |
| 4,144,319 | 3/1979 | Willer et al. | 424/45 |
| 4,160,819 | 7/1979 | Willer et al. | 424/45 |
| 4,199,575 | 4/1980 | Gunther | 424/217 |
| 4,259,318 | 3/1981 | Duhé et al. | 424/94 |
| 4,344,965 | 8/1982 | Stone | 424/310 |
| 4,428,965 | 1/1984 | Elsohly et al. | 424/311 |
| 4,609,544 | 9/1986 | Herlihy | 424/59 |
| 4,738,956 | 4/1988 | Scott et al. | 514/179 |
| 4,861,584 | 8/1989 | Powell, Jr. et al. | 424/79 |
| 5,011,689 | 4/1991 | Misenko | 424/195.1 |
| 5,017,361 | 5/1991 | Powell, Jr. et al. | 424/46 |
| 5,036,050 | 7/1991 | Audhya et al. | 514/17 |
| 5,049,580 | 9/1991 | Crouthamel | 514/424 |
| 5,086,075 | 2/1992 | De Villez | 514/714 |

FOREIGN PATENT DOCUMENTS

| | | |
|---|---|---|
| 189862 | 1/1974 | Canada . |

OTHER PUBLICATIONS

Jones et al., "Topical Nonsteroidal Antipsoriatic Agents. 1. 1,2,3,4–Tetraoxygenated Naphthalene Derivaties[1]", J. Med. Chem, 1986, 29, 1504–1506.

Hughes et al., "Safety and Pharmacokinetics of 566C80, a Hydroxynaphthoquinone with Anti–*Pneumocystis carinii* Activity: A Phase I Study in Human Immunodeficiency Virus (HIV)–Infected Men", The Journal of Infectious Diseases, 1991; 163:843.

Lepoittevin et al., "Allergic contact dermatitis caused by naturally occurring quinones*", Pharmaceutisch Weekblad Scientific editions 13(3), 119–122 (1991).

Schulz et al., "The Sensitizing Capacity of Naturally Occurring Quinones*.–Experimental Studies in Guinea Pigs", Arch. Derm. Res. 258, 41–52 (1977).

Wheeler et al., "Melanin biosynthesis and the metabolism of flaviolin and 2–hydroxyjuglone in *Wangiella dermatitidis*", Arch. Microbiol (1985) 142:234–241.

Vietmeyer, "Science has got its hand on poson ivy, oak and sumac", Smithsonian, Aug., 1985, pp. 89–95.

Zink et al., "The effect of jewel weed in preventing poison ivy dermatitis", Journal of Wilderness Medicine 2, 178–182 (1991).

The Merck Index, Twelfth Edition, 5406.Lawsone, p. 922, 1996.

The Merck Index, Twelfth Edition, 5282.Juglone, p. 898, 1996.

*Primary Examiner*—Leonard Schenkman
*Attorney, Agent, or Firm*—Fish & Richardson, P.C.

[57] ABSTRACT

A method useful for the treatment of itching is disclosed. The method comprises applying an effective amount a 1,4-naphthoquinone to the affected area of the skin. The 1,4-naphthoquinone is hydroxy or keto at the 2 position or the 3 position, or a juglone. A composition comprising an effective amount of the 1,4-naphthoquinone, and a kit for conducting the method are also provided.

28 Claims, No Drawings

METHOD FOR THE TREATMENT OF ITCHING

RELATED APPLICATION INFORMATION

This application relates to provisional application Ser. No. 60/015,029, filed Apr. 8, 1996.

BACKGROUND OF THE INVENTION

This invention relates to a method, compositions and kits for the treatment of itching.

Itching is a symptom, commonly associated with dermatitis, caused by various insults in mammals. Insect bites, exposure plants or foods, skin diseases and skin disorders are examples of the kind of insult which can result in itching. Pruritus may also be caused by systemic diseases (such as obstructive bilary disease) or be of unknown origin.

Itching of the skin caused by foods, plants or other insults discussed above is frequently caused by the direct contact of irritants and the skin. However, indirect transfer of irritants, such as by ingestion of foods etc., and transport internally through the body to the skin is also believed to occur and to lead to itching. In the art, compounds which induce itching, dermatitis, or both can be referred to as allergens or allergenic compounds, sensitizing or sensitizer compounds, elicitor compounds, irritants or other similar names. In this description, no distinction is made between any of these names, but for convenience they are generally referred to simply as "irritants."

Plant irritants are exemplary of the irritants which come into contact with the skin and lead to itching. For example, itching is commonly associated with contact dermatitis induced by irritants present in plants of the Anacardiaceae and Ginkgoaceae families. Included among these plants are the Toxicodendrons, e.g., poison ivy (*T. radicans*), Eastern poison oak, (*T. quercifolium*), poison sumac (*T. vernix*), and Western poison oak (*T. diversilobum*). Also included are manzanillo (*Rhus striata*), Japanese lac (*R. verniciflua*), Mango tree (*Mangifera indica*), India ink tree, (*Semicarpus anacardum*), ginko tree (*Ginko biloba* L.), and the cashew tree (*Anacardium occidentale*).

One such group of plant-borne irritants is a mixture of alkyl-catechols known as the urushiols. Urushiols are present in, e.g., poison ivy and Japanese lac, and are known to induce the contact dermatitis commonly known as "poison ivy" rash. One to two million people are said to be afflicted with varying degrees of poison ivy rash each year. It has been estimated that as many as 150,000 working days are lost annually to urushiol induced contact dermatitis. (Vietmeyer, N. Smithsonian Vol. 16, no. 5, August 1985).

The mechanism of action of urushiols in inducing contact dermatitis has been described in the literature. (See, e.g., Lepoittevin, J-P. and Benezra, C. Allergic contact dermatitis caused by naturally occurring quinones. Pharm. Weekbl [Sci] (Netherlands) Jun. 21, 1991. 13(3):119–122). It is believed that the mechanism of action of the urushiols may be general to many irritants that lead to itching. Briefly, the process leading to urushiol-induced contact dermatitis, or poison ivy rash, is reported to be as follows. Urushiols are transmitted from the plant to the skin and are oxidized in vivo to ortho-quinones. The ortho-quinones are thought to interact with proteins and form quinone-protein conjugates which act as the actual antigens. Next, the conjugates are reported to be presented to inexperienced T-lymphocytes by epidermal macrophages. The exposed lymphocytes can develop into immunologically competent lymphocytes which are capable of reacting to subsequent exposure to the urushiols. At this point a mammal is said to be sensitized to the urushiols. The subsequent exposure of these competent lymphocytes to urushiol (ortho-quinone)-protein conjugates is thought to lead to the release of lymphokines and the manifestation of urushiol induced contact dermatitis—the poison ivy rash.

Poison ivy rash starts with a reddening of the skin and itching. The itching intensifies with time and watery blisters appear. The itching typically causes afflicted mammals to scratch the affected area. This can delay healing and can spread urushiols to a wider area of the skin or other parts of the body.

The widespread occurrence of poison ivy induced dermatitis has led to the proposal of many treatments to prevent or alleviate the symptoms of the poison ivy rash. Methods reported to prevent the rash include the use of desensitizing materials, urushiol absorbing materials, and forming protective layers on the skin to block irritants. Reportedly useful methods for alleviating symptoms include applying plant extracts, corticosteroids, and enzymes including catechol oxygenase or p-diphenol oxidase, washing irritants from the skin with polyglycol ethers, thymopentin therapy and the use of topical anesthetics. (Examples of reportedly useful methods of treatment to prevent or alleviate symptoms of contact dermatitis can be found in U.S. Pat. Nos. 5,086,075; 5,049,580; 5,036,050; 5,017,361; 5,011,689; 4,861,584; 4,738,956; 4,344,965; 4,428,965; 4,259,318; 4,199,575; 4,160,819; 4,144,319; 4,141,966; 4,137,301; 4,112,067; 4,002,737 and 3,974,281; Canadian Patent No. 1032473; and European Patent No. 0 311 963 A1, all of which are incorporated herein by reference.)

In addition, there are numerous purportedly effective ethnobotanical treatments for alleviating itching, including the itching associated with poison ivy. However, the use of plant material or crude plant extracts in therapeutic methods, compositions and kits can have undesirable drawbacks. These include the presence in the final composition of unknown or undesirable irritants that can exacerbate itching, dermatitis, or both. Compositions can also vary widely in components and component concentrations depending on factors such as method of preparation or plant growth conditions, e.g., soil type, nutrient supply, season, water supply, etc. Other drawbacks and dangers of applying plant materials to dermatitis include the potential presence of excess bulk; irritating bits of leaf, stem or root; soil; insect parts and infectious microorganisms.

One such ethnobotanical cure purported that jewelweed was an effective plant in the treatment of itching associated with poison ivy rash. However, publications have dismissed the value of treatments using this plant (Zink, B. J. et al. 1991. Journal of Wilderness Medicine, Vol. 2:178–182).

SUMMARY OF THE INVENTION

An aspect of this invention is a method for the treatment of itching in a mammal. The method includes administering a topical formulation containing an effective amount of a 1,4-naphthoquinone to relieve itching. The 1,4-naphthoquinones of the invention are of the formula:

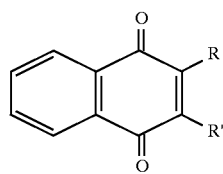

wherein either R or R' is a hydroxyl or a methoxy group. The position occupied by the other one of R or R', can be, for example, hydrogen, hydroxyl, methyl, methoxy, quaternary amine, a cycloalkyl group containing 3 to 7 carbon atoms, and alkyl, 1-alkylaminoalkyl, 1-alkenyl or alkanoyl groups of 2 to 3 carbons. The aromatic ring of the 1,4-naphthoquinone can be unsubstituted or substituted with one or more groups which do not adversely affect the effectiveness of the 1,4-naphthoquinone. A pharmaceutically acceptable salt of the compound can be used. A pharmaceutically acceptable carrier can also be included in the formula. The method can be conducted on a variety of animals. In a preferred embodiment the method is conducted on a human.

In a preferred embodiment of this method the 1,4-naphthoquinone is a natural or synthetic compound. In other preferred embodiments the 1,4-naphthoquinone is a lawsone, a lapachol, a phthiocol, a 2-hydroxy-juglone or a 3-hydroxy-juglone. In a most preferred embodiment the 1,4-naphthoquinone is a lawsone, also known as 2-hydroxy-1,4-naphthoquinone.

In certain preferred embodiments the 1,4-naphthoquinone is present in a carrier at a concentration from at least about 20 to about 100 parts per million or from about 50 to about to 100 parts per million. In certain preferred embodiments, the carrier is aqueous.

An aspect of this invention is a composition for the treatment of itching in a mammal. The composition can be conveniently formulated as a topical composition containing an effective amount of a 1,4-naphthoquinone of the formula

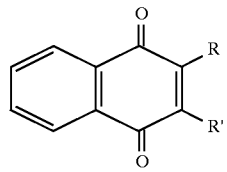

where either R or R' is a hydroxyl or a methoxy group. The other one of R or R' can be, for example, hydrogen, hydroxyl, methyl, methoxy, quaternary amine, a cycloalkyl group containing 3 to 7 carbon atoms, and alkyl, 1-alkylaminoalkyl, 1-alkenyl or alkanoyl groups of 2 to 3 carbons. The aromatic ring of the 1,4-naphthoquinone can be unsubstituted or substituted with one or more groups which do not adversely affect the effectiveness of the 1,4-naphthoquinone. A pharmaceutically acceptable salt of the compound can be used. The compound can be combined with a pharmaceutically acceptable carrier.

In certain preferred embodiments of the composition the 1,4-naphthoquinone can be a lawsone, a lapachol, a phthiocol, a 2-hydroxy-juglone or a 3-hydroxy-juglone. In a most preferred embodiment the 1,4-naphthoquinone is a lawsone.

In other preferred embodiments of the composition the 1,4-naphthoquinone is present in a carrier at a concentration from at least about 20 to about 100 parts per million or from about 50 to about to 100 parts per million. In certain preferred embodiments the carrier is an aqueous carrier.

An aspect of this invention is a kit for the treatment of itching by applying a topical composition containing an effective amount of a 1,4-naphthoquinone. The kit has at least one predetermined amount of a 1,4-naphthoquinone of the formula:

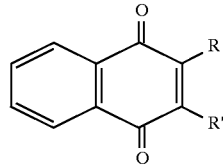

where either R or R' is a hydroxyl or a methoxy group. The other one of R or R' can be hydrogen, hydroxyl, methyl, methoxy, quaternary amine, a cycloalkyl group containing 3 to 7 carbon atoms, and alkyl, 1-alkylaminoalkyl, 1-alkenyl or alkanoyl groups of 2 to 3 carbons. The aromatic ring of the 1,4-naphthoquinone can be unsubstituted or substituted with one or more groups which do not adversely affect the effectiveness of the 1,4-naphthoquinone. A pharmaceutically acceptable salt of a naphthoquinone can be used. The kit also includes at least one predetermined amount of a pharmaceutically acceptable carrier. The kit also includes instructions to prepare a topical composition containing an effective amount of a 1,4-naphthoquinone by mixing at least one of the amounts of the 1,4-naphthoquinone with at least one of the amounts of a carrier before applying the composition to the skin of a mammal.

In a preferred embodiment of this kit the composition is formulated in an aqueous carrier. In a preferred embodiment the 1,4-naphthoquinone can be a lawsone, a lapachol, a phthiocol, a 2-hydroxy-juglone or a 3-hydroxy-juglone.

In other preferred embodiments of this kit the 1,4-naphthoquinone is present in a carrier at a concentration from at least about 20 to about 100 parts per million or from about 50 to about to 100 parts per million.

An aspect of this invention is a kit for the treatment of itching in a mammal by applying a topical composition containing an effective amount of a 1,4-naphthoquinone to the skin of the mammal. The kit has at least one predetermined amount of a 1,4-naphthoquinone of the formula

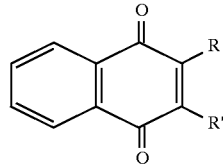

where either R or R' is a hydroxyl or a methoxy group. The other one of R or R' can be hydrogen, hydroxyl, methyl, methoxy, quaternary amine, a cycloalkyl group containing 3 to 7 carbon atoms, and alkyl, 1-alkylaminoalkyl, 1-alkenyl or alkanoyl groups of 2 to 3 carbons. The aromatic ring of the 1,4-naphthoquinone can be unsubstituted or substituted with one or more groups which do not adversely affect the effectiveness of the 1,4-naphthoquinone. A pharmaceutically acceptable salt of a 1,4 naphithoquinone may be used. This kit includes instructions to prepare the topical composition by mixing at least one predetermined amount of 1,4-naphthoquinone with a predetermined amount of an aqueous carrier before applying the composition to the skin of a mammal.

In a preferred embodiment of this kit the composition is formulated in an aqueous carrier. In certain preferred embodiments the 1,4-naphthoquinone can be a lawsone, a lapachol, a phthiocol, a 2-hydroxy-juglone or a 3-hydroxy-juglone.

In other preferred embodiments of this kit the 1,4-naphthoquinone is present in a carrier at a concentration from at least about 20 to about 100 parts per million or from about 50 to about to 100 parts per million.

In preferred embodiments of the kits described above, the 1,4-naphthoquinone is provided in a tablet.

As noted, also preferred in the kits, methods and compositions described above are aqueous carriers. As examples these carriers can be water soluble or water based carriers such as gels, creams and sols.

Certain preferred embodiments of the method, kit or composition of this invention utilize a 1,4-naphthoquinone wherein the aromatic ring is substituted with one or more groups. The substitutions can be selected from Cl, Br, F, phosphates, nitrates, sulphates, methoxy, carboxy, carboxylates or carboxy-lower alkyl groups where the alkyl group is 2 to 3 carbons, hydroxy or hydroxylates, quaternary amines, glucosyl or glucosylamine groups, branched or straight chain alkyl groups of 2 to 3 carbons and methyl groups. These and other substitutions can be present with the limitation that the substitution does not abolish the effectiveness of the 1,4-naphthoquinone.

Another aspect of this invention is a method for the treatment of itching in a mammal that includes administering to the affected area of the skin of a mammal in need of such treatment a topical formulation containing an effective amount of a juglone to relieve itching. The juglone is of the formula:

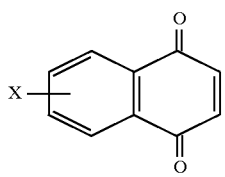

wherein X can be, for example, hydrogen, hydroxyl, methyl, methoxy, quaternary amine, ketone, a cycloalkyl group containing 3 to 7 carbon atoms, and alkyl, 1-alkylaminoalkyl, 1-alkenyl or alkanoyl groups of 2 to 3 carbons and wherein the substitutions of the aromatic ring the juglone do not adversely affect the effectiveness of the juglone. A pharmaceutically acceptable salt of the compound can be used. A pharmaceutically acceptable carrier can also be used. The method can be conducted on a variety of animals. In a preferred embodiment the method is conducted on a human.

In a preferred embodiments of this method the juglone is a natural or synthetic compound and can be selected from the group consisting of 5-hydroxy-1,4 naphthquinones, 6-methyl juglone, and 8-ketojuglone. In a preferred embodiment of this method, juglone is 5-hydroxy-1,4 naphthoquinone.

In certain preferred embodiments the juglone is present in a carrier at a concentration from at least about 20 to about 100 parts per million or from at least about 50 to about to 100 parts per million. In certain preferred embodiments carrier is an aqueous carrier.

An aspect of this invention is a composition for the treatment of itching in a mammal. The composition can be conveniently formulated as a topical composition containing an effective amount of a juglone of the formula:

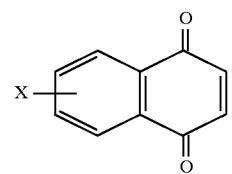

where X can be, for example, hydrogen, hydroxyl, methyl, methoxy, quaternary amine, ketone, a cycloalkyl group containing 3 to 7 carbon atoms, and alkyl, 1-alkylaminoalkyl, 1-alkenyl or alkanoyl groups of 2 to 3 carbons and wherein the substitutions of the aromatic ring of the juglone can do not adversely affect the effectiveness of the juglone. A pharmaceutically acceptable salt can be used. A pharmaceutically acceptable carrier is used. In preferred embodiments of this composition the juglone is selected from the group consisting of 5-hydroxy-1,4 naphthoquinones, 6-methyl juglone, and 8-ketojuglone. In a preferred embodiment of this composition, juglone is 5-hydroxy-1,4 naphthoquinone.

In other preferred embodiments of the composition the juglone is present in a carrier at a concentration from at least about 20 to about 100 parts per million or from about 50 to about to 100 parts per million. In certain preferred embodiments the carrier is an aqueous carrier.

An aspect of this invention is a kit for the treatment of itching by applying a topical composition containing an effective amount of a juglone. The kit has at least one predetermined amount of a juglone of the formula:

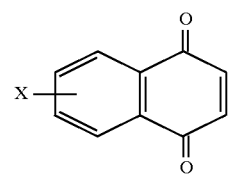

where X can be hydrogen, hydroxyl, methyl, methoxy, quaternary amine, ketone, a cycloalkyl group containing 3 to 7 carbon atoms, and alkyl, 1-alkylaminoalkyl, 1-alkenyl or alkanoyl groups of 2 to 3 carbons, and wherein the substitutions of the aromatic ring of the juglone do not adversely affect the effectiveness of the juglone. A pharmaceutically acceptable salt can be used. The kit also includes at least one predetermined amount of a pharmaceutically acceptable carrier. The kit also includes instructions to prepare a topical composition containing an effective amount of the juglone by mixing at least one of the amounts of the juglone with at least one of the amounts of a carrier before applying the composition to the skin of a mammal.

In preferred embodiments of the kit, the juglone is selected from the group consisting of 5-hydroxy-1,4 naphthoquinones, 6-methyl juglone, and 8-ketojuglone. In a preferred embodiment of this composition, juglone is 5-hydroxy-1,4 naphthoquinone.

In other preferred embodiments of this kit the juglone is present in a carrier at a concentration from at least about 20 to about 100 parts per million or from about 50 to about to 100 parts per million.

An aspect of this invention is a kit for the treatment of itching in a mammal by applying a topical composition containing an effective amount of a juglone to the skin of the mammal. The kit has at least one predetermined amount of a juglone of the formula

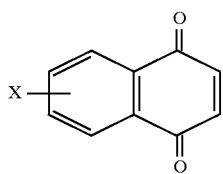

where X can be hydrogen, hydroxyl, methyl, methoxy, quaternary amine, ketone, a cycloalkyl group containing 3 to 7 carbon atoms, and alkyl, 1-alkylaminoalkyl, 1-alkenyl or alkanoyl groups of 2 to 3 carbons, and wherein the substitutions of the aromatic ring of the juglone do not adversely affect the effectiveness of the juglone. A pharmaceutically acceptable salt may be used. This kit includes instructions to prepare the topical composition by mixing at least one predetermined amount of juglone with a predetermined amount of an aqueous carrier before applying the composition to the skin of a mammal.

In preferred embodiments of the kit, the juglone is selected from the group consisting of 5-hydroxy-1,4 naphthoquinones, 6-methyl juglone, and 8-ketojuglone. In a preferred embodiment of this composition, juglone is 5-hydroxy-1,4 naphthoquinone.

In a preferred embodiment of this kit the composition is formulated in an aqueous carrier.

In other preferred embodiments of this kit the juglone is present in a carrier at a concentration from at least about 20 to about 100 parts per million or from about 50 to about to 100 parts per million.

In preferred embodiments of the kits described above the juglone is provided in a tablet.

As noted, also preferred in the kits, methods and compositions described above are aqueous carriers. As examples these carriers can be water soluble or water based carriers such as gels, creams and sols.

Certain preferred embodiments of the method, kit or composition of this invention utilize a juglone wherein the aromatic ring is substituted with one or more groups. The substitutions can be selected from Cl, Br, F, phosphates, nitrates, sulphates, methoxy, carboxy, carboxylates or carboxy-lower alkyl groups where the alkyl group is 2 to 3 carbons, hydroxy or hydroxylates, quaternary amines, glucosyl or glucosylamine groups, branched or straight chain alkyl groups of 2 to 3 carbons and methyl. These and other substitutions can be present with the limitation that the substitution does not abolish the effectiveness of the juglone.

Other advantages and features of this invention will be apparent from the description and the claims.

DEFINITIONS

As used herein a "pharmaceutically acceptable carrier" or "excipient" refers to a carrier or excipient useful in a composition of this invention, which carrier does not substantially interfere with the action of a compound useful in this invention and is acceptable in a topical composition for application to the skin of mammals. This includes carriers or excipients used in compositions which are applied to the skin directly or are used to make further compositions for direct topical application to the skin. For example, a first carrier or excipient can be used in a composition formulated to provide a compound in a predetermined amount for dissolution in a second carrier, such as an aqueous solution, to make a topical composition for application to the skin.

As used herein a "composition" refers to any compound useful in this invention or any combination or formulation of a pharmaceutically acceptable carrier or excipient and a compound useful in the invention. Depending on the intended mode of use of compositions, the compositions can be in the form of solid, semi-solid or liquid dosage forms, such as, for example, tablets, capsules, pills, powders, granules, crystals, liquids, suspensions, or the like, preferably in unit-dosage forms suitable for administration of relatively precise dosages. The compositions can include a conventional pharmaceutically acceptable carrier or excipient and, in addition, can include other medical agents, pharmaceutical agents, carriers, etc. The compositions can be topical compositions or compositions formulated for the ultimate preparation of topical compositions. In certain cases compositions can include plant materials used as carriers. In these instances the plant material can be mixed with a compound useful in the method of this invention if the compound is derived from a source other than the actual plant material used as the carrier.

Useful in the invention are a class of p-naphthoquinone compounds generally characterized by the formula:

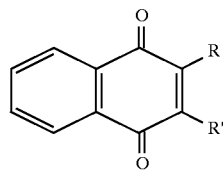

wherein either R or R' is a hydroxyl or a methoxy group and the other one of R or R' can be hydrogen, hydroxyl, methyl, methoxy, quaternary amine, a cycloalkyl group containing 3 to 7 carbon atoms, and alkyl, 1-alkylaminoalkyl, 1-alkenyl or alkanoyl groups of 2 to 3 carbons, and wherein the aromatic ring of said 1,4-naphthoquinone is unsubstituted or substituted with one or more groups which do not adversely affect the effectiveness of the 1,4-naphthoquinone, or a pharmaceutically acceptable salt thereof.

Also useful in the invention are a class of naphthoquinones referred to as juglones generally characterized by the formula:

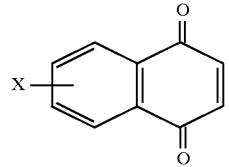

wherein X can be for example, hydrogen, hydroxyl, methyl, methoxy, quaternary amine, ketone, a cycloalkyl group containing 3 to 7 carbon atoms, and alkyl, 1-alkylaminoalkyl, 1-alkenyl or alkanoyl groups of 2 to 3 carbons and wherein the substitutions of the aromatic ring the juglone do not adversely affect the effectiveness of the juglone.

As used herein an "effective amount" of the compounds or invention is an amount which relieves or ameliorates the itching associated with a given condition in 20% or more of subjects presenting that condition.

As used herein a "natural" compound refers to a compound or irritant that is partially or completely isolated from or purified from a biological material. The partial or complete isolation or purification can be by any of a variety of physical, chemical or other procedures known in the art. For present purposes, the partially or completely isolated or purified compound is still considered a natural compound. A salt of the partially or completely isolated compound is also considered a natural compound.

As used herein a "synthetic" compound refers to a compound or irritant created or derived through processes that can be referred to as chemical synthesis, chemical reaction, chemical derivation, biochemical conversion and the like, or combinations thereof. A synthetic compound can be structurally the same as, or the chemical equivalent of, a natural compound. A synthetic compound can be derived from a natural compound via synthetic processes.

As used herein "treatment" refers to a method or process of alleviating, ameliorating, curing or preventing/itching.

DESCRIPTION OF THE PREFERRED EMBODIMENTS

It has been discovered that 1,4-naphthoquinones, wherein the hydroxyl group is at position 2 or 3, and juglones (a class of 1,4 naphthoquinones that are not so substituted) are useful in alleviating the itching generally associated with any irritation or allergic reaction. These compounds are useful in alleviating pruritus, e.g., the itching associated with contact dermatitis. For example, these compounds are useful in alleviating the itching induced by ortho-quinone forms of various cyclic irritants or from itching caused by any irritant or allergic reaction.

It is reported in the art that urushiols are members of a class of irritant compounds that exist as, or are oxidized in vivo to, ortho-quinones and that these ortho-quinone forms are responsible for the allergenic nature of these compounds. Urushiols appear to be the most studied of these irritants due to the impact of the poison ivy induced contact dermatitis in humans. It is also generally reported that the ortho-quinone forms of the urushiols and other irritants are important in the overall pathology of contact dermatitis.

Without wishing to be bound by any particular theory, it is postulated that the 1,4-naphthoquinone compounds useful as taught herein act by blocking an activity or binding of ortho-quinones and other irritants that causes itching and other symptoms of contact dermatitis. It is possible that the 1,4-naphthoquinones can alleviate itching by blocking the interaction of ortho-quinones and other irritants with histamine receptors, or by otherwise inactivating histamine receptors.

A general class of 1,4-naphthoquinones compounds useful in the present invention are characterized by a hydroxyl group at the 2 or 3 position. This general class of 1,4-naphthoquinones can exist in equilibrium with 1,2-diketo or 2,3-diketo forms. For example, a 2-hydroxy-1,4-naphthoquinone can exist in equilibrium with the 1,2-diketo as:

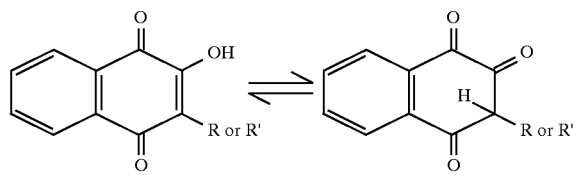

The diketo forms can mimic ortho-quinones and other irritants that cause itching and trigger contact dermatitis, e.g., urushiols. The 1,4-naphthoquinones are thereby postulated to compete with and or block the activity or binding of allergenic ortho-quinones and other irritants.

A useful class of compounds in this invention are juglones, for example, 5-hydroxy-1,4 naphthoquinone. This compound is similar in action to the lawsone derivatives (2-hydroxy-1,4 naphthoquinone) in structure and will react with proteins in the same manner. Essentially, in nature, the reaction of the keto forms of both will react with the amino groups of proteins even though the spacing between the formed carbonyls is different. In the lawsone the 2-hydroxy becomes a carbonyl and the 1,2-dicarbonyl derivative is bioactive. In solution, the 5-hydroxy group of juglone becomes a carbonyl. The 4,5-dicarbonyl is again bioactive, even though there is one ring carbon between the two carbonyls. It has been observed that this compound (juglone) has a more powerful anti-itch property than lawsone. Juglone is a natural product found in walnuts (genus Juglans).

Many of the general class of 1,4-naphthoquinones described herein are not seen to be generally sensitizing in mammals either generally or at effective concentrations useful in this invention. For example, lawsone, a 2-hydroxy-1,4-naphthoquinone, and its derivatives have been used in contact with human skin for hundreds of years as hair coloring. Lawsone and derivatives are also used applied to the skin as skin colorant or protectant from UV radiation as described in, for example, U.S. Pat. Nos. 3,920,808, 4,228, 151 and 4,832,943, incorporated herein by reference. Lapachol, a 3-hydroxy-1,4-naphthoquinone is also known to exhibit very low sensitizing activity (see e.g., Lepoittevin and Benezra, incorporated above). Another example is phthiocol, a compound found in *Tabebuia avellanedae* Lor. ex Griseb. and now also considered to be an oxidative artifact of K vitamin synthesis. Phthiocol is also believed to be non-sensitizing or allergenic at concentrations that would be effective to relieve itching.

It should be noted that the subset of 1,4-naphthoquinones where both the 2 and 3 positions are hydroxyl can be photosensitizers. If these compounds are used one should be aware that exposure of skin to, for example, sunlight, treated with these compounds can lead to inflammation and increased discomfort.

The 1,4-naphthoquinone compounds useful to alleviate itching as described herein can form dimers, or other oligomers, in solution. Dimers, or other oligomers, can be formed by interactions between carbons 5–10 of two 1,4-naphthoquinone molecules. (see, e.g., Lepoittevin and Benezra, incorporated above). No difference in the action of the compounds useful in this invention has been noted due to the presence of oligomers.

Similarly, these 1,4-naphthoquinone compounds can exist in nature, and be isolated or purified therefrom as 1-glucosyl-, 4-glucosyl- or 1,4-diglucosyl forms. For example, 2-hydroxy-juglone (2,6-dihydroxy-p-naphthoquinone) can occur as a hydrojuglone glycoside (Schultz, K. H. et al. 1977. The sensitizing capacity of naturally occurring quinones—Experimental studies in Guinea pigs. I. Naphthoquinones and related compounds. Arch. Derm. Res. 258:41–52. incorporated herein by reference). 1,4-Naphthoquinones useful in this invention can be natural compounds or synthetic compounds—the latter including synthetic derivatives made from natural compounds. Synthetic and natural compounds can be equivalently used in this invention. For example, lawsone, 2-hydroxy-1,4-naphthoquinone, is commonly isolated or purified from *Lawsonia alba* and related species, e.g. *L. inermis*. The chemical synthesis of lawsone is also known and synthetic lawsone is commercially available (e.g., from Sigma Chemical Co., St. Louis, Mo. 1994 Cat. No. H0508). In a method, kit, or composition of this invention, either natural or synthetic lawsone can be used.

As will be recognized by those skilled in the art, derivatives of the 1,4-naphthoquinones described herein can be made and used in the method, compositions and kits of this invention. The 1,4-naphthoquinones have an aromatic ring that can optionally carry one or more substituents X:

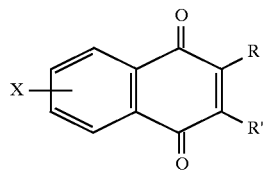

wherein either R or R' may be a hydroxyl or a methoxy group and the other one of R or R', is selected from the group consisting of hydrogen, hydroxyl, methyl, methoxy, quaternary amine, cycloalkyl group containing 3 to 7 carbon atoms, and alkyl, 1-alkylaminoalkyl, 1-alkenyl or alkanoyl groups of 2 to 3 carbons, and wherein the aromatic ring of the 1,4-naphthoquinone is unsubstituted. Alternatively, is substituted with one or more groups which do not adversely affect the effectiveness of the 1,4-naphthoquinone, thus the ring substituent X, ca be any ring substitution which does not adversely affect the effectiveness the 1,4-naphthoquinone, e.g., a ring substitution can alter, but not abolish the therapeutic activity of the 1,4-naphthoquinone compound. The ring substituent X, can be chosen from a variety of chemical groups. For example, X can be selected from halogens such as Cl, Br & F, or from oxygenated groups including phosphates, nitrates, sulphates, or from methoxy, carboxy, carboxylate or carboxy-lower alkyl group, or from hydroxy or hydroxylates, or from quaternary amines, or from glucosyl or glucosylamine, or from a variety of branched or straight chain alkyl groups or methyl.

One or more ring substitutions can be a useful means to increase or decrease solubility as deemed desirable for suitable use in this invention. As is apparent to one skilled in the art, a hydrophilic substituent should increase solubility while a hydrophobic substituent should decrease solubility.

Herein, these derivatives are referred to as being a member of the 1,4-naphthoquinone of the source material, or having a chemical backbone thereof. For example, a ring substitution derivative of lawsone are referred to as one of the "lawsones," a ring substitution derivative of lapachol are referred to as one of the "lapachols," and so on. In cases of named compounds that carry ring substituents as named, an example being juglone having a hydroxyl group on the aromatic ring, a derivative is a compound with at least one additional ring substitution.

EXAMPLES

Example 1

Compositions

For solid compositions, compounds useful in this invention can be provided separately or can be compounded with conventional nontoxic solid carriers such as, for example, pharmaceutical grades of mannitol, lactose, starch, magnesium stearate, talcum, cellulose, glucose, sucrose, magnesium carbonate, and the like. Liquid pharmaceutically-administrable topical compositions can be prepared, for example, by dissolving the a 1,4-naphthoquinone and optional pharmaceutical adjuvants in an aqueous carrier, such as, for example, water, aqueous dextrose, and the like, to thereby form a solution or suspension. If desired, the pharmaceutical composition to be administered can also contain minor amounts of nontoxic auxiliary substances such as pH buffering agents and the like, for example, sorbitan monolaurate, triethanolamine, sodium acetate, triethanolamine oleate, etc. Compositions can also be prepared as creams, sols or gels in aqueous bases. Actual methods of preparing such dosage forms are known, or will be apparent, to those ordinarily skilled in this art; see, for example, Remington's Pharmaceutical Sciences, Mack Publishing Company, Easton, Pa., 16th Ed., 1982, which is incorporated herein by reference, and like references in the pharmaceutical sciences.

A 1,4-naphthoquinone or derivative may be solubilized in an appropriate solvent, e.g., 5–10% ethanol when preparing a compound.

1,4-Naphthoquinones can vary in their stability in a topical composition. As when formulating any composition, compositions of this invention should be tested for shelf-life. For example, the composition used in a clinical trial described below is 2-hydroxy-1,4-naphthoquinone mixed in water. It has been found that this composition is most effective if used within about three days of mixing. It has been noted that once mixed into water, the effectiveness of the topical composition gradually decreases over about three days and then levels off.

Example 2

Method of Treatment of Itching

The method of this invention is simply performed by applying a topical composition containing an effective amount of an 1,4-naphthoquinone to the skin of a mammal in need of treatment because the mammal is afflicted with pruritus, which can also be associated with dermatitis.

The amount of a 1,4-naphthoquinone which is effective can be determined via standard experimental techniques known in the art of dosage formulation. Briefly, one can begin by preparing topical compositions containing from 0.1 to 100.0 ppm (parts per million) of a particular 1,4-naphthoquinone in a pharmaceutically acceptable carrier. The topical compositions are then tested by applying them to the skin of an afflicted mammal and scoring the relief from itching provided by the composition. One can proceed to test concentrations of a 1,4 naphthoquinone above and below the aforementioned ranges as necessary to arrive at an effective amount, i.e., one can prepare compositions ranging up to 200, 500, 750 or 1000 ppm for compounds or formulations that are relatively less effective and down to 0.05, 0.025, 0.01, 0.0075, 0.005, 0.0025 or more with compounds or formulations that are relatively more effective. The concentration may also be determined by weight of the compound, e.g., not less than 2–10 μg/ml.

For example, if the mammal is a guinea pig a topical composition can be applied to a shaved portion of the mammal's skin in which a contact dermatitis has been induced and the animal can be observed for behavioral changes indicating relief from itching. If the mammal is a human, the topical composition can be applied to the skin of the person and the person can be asked directly to subjectively assess the relief conferred by the composition.

Once the range of effective amounts has been determined, a topical composition containing an effective amount can be prepared on demand for conducting the method of treatment of this invention.

Example 3

Kits to Facilitate Performing the Method of Treatment

A kit is a useful means of conducting the method of treatment described herein. A kit can provide a container in which at least one, or a plurality, of a predetermined amount of a 1,4-naphthoquinone is provided to a user to facilitate performing the method. The user can employ the kit to perform the method on themselves or on another.

The predetermined amount of 1,4-naphthoquinone compound can be conveniently provided in many different formulations in a kit. The 1,4-naphthoquinone can be provided dry to allow the user to prepare the topical composition shortly before use. If dispensed under prescription, a pharmacist could prepare the topical composition shortly before dispensing to a patient. If the compound is not provided in a dry form, a topical composition can be conveniently formulated in a pharmaceutically acceptable carrier suitable to use with the particular 1,4-naphthoquinone. For example, if lawsone is the 1,4-naphthoquinone, water or a water soluble gel, sol or cream is an acceptable carrier. The addition of water allows the hydroxy and diketo states of lawsone to be in equilibrium.

Several convenient compositions of 1,4-naphthoquinone are particularly useful. A powdered composition of or containing 1,4-naphthoquinone can be used to provide predetermined amounts of 1,4-naphthoquinone. It is useful to provide these compositions in kits in containers of various types including pouches, capped vials or bottles, spray bottles etc. If a pouch is provided the user can prepare a topical composition by adding the contents of the pouch to an amount of an liquid carrier. If a container is provided in the kit the user can prepare a topical composition simply by adding an aqueous carrier to the container and shaking. Various other means of providing powdered formulations for the preparation of topical compositions are known, or will be apparent, to those of ordinary skill in the art.

When using a kit, a desired final concentration of a 1,4-naphthoquinone in a topical composition can be realized in many ways. For example, the final concentration can be achieved by adding a predetermined amount of aqueous carrier to the composition, e.g., a container can contain a composition and have a fill line to indicate that a predetermined amount of aqueous carrier should be added. Instructions can be provided directing a user to add a particular amount of an aqueous carrier to a particular amount of a composition.

Alternatively, a final concentration can be achieved by relying on the solubility of a particular 1,4-naphthoquinone in a topical composition. For example, lawsone is soluble in water at up to about 100 micrograms per milliliter. If the particular 1,4-naphthoquinone is lawsone and the topical composition is lawsone in water, then the solubility limit of lawsone in the carrier water can limit the final concentration of the 1,4-naphthoquinone in the topical composition. It should be noted that additional components in a topical composition can affect the solubility of the 1,4-naphthoquinone. Therefore, if one desires to rely on solubility limits to determine the final concentration of the 1,4-naphthoquinone in a topical composition a simple solubility test can be performed with the particular 1,4-naphthoquinone in a particular topical composition.

Example 4

Dissolving tablets

A 1,4-naphthoquinone can be formulated into tablets that will dissolve in an aqueous carrier to create a topical composition containing an effective amount of an 1,4-naphthoquinone. The tablets can be added to an amount of an aqueous carrier and mixed to dissolve and form a topical composition. Effervescent tablet formulations can also be used and can avoid an need to mix to form the topical composition. As described above, the final concentration can be controlled by adding a predetermined amount of a formulation to a predetermined amount of carrier, by directions or by solubility.

Example 5

Clinical Evidence of Lawsone Effectiveness

A clinical trial was held to assess the effectiveness of 1,4-naphthoquinones in the treatment of itching. Lawsone, 2-hydroxy-1,4-naphthoquinone was chosen as the 1,4-naphthoquinone tested in the clinical trial because it is readily available and has been used uneventfully in contact with human skin for cosmetic purposes. Other 1,4-naphthoquinones can be tested in a similar manner.

Lawsone was obtained as an orange powder from Sigma Chemical Co., St. Louis, Mo. 1994 catalog number H0508. The powder was divided into containers in predetermined amounts of about 10 milligrams for the convenience of the subjects.

The subjects were human volunteers presenting with symptoms of contact dermatitis caused by poison ivy. The volunteers gave their informed consent to the treatment tested in the clinical trial.

The subjects were provided with the 1,4-naphthoquinone and directions to prepare a topical composition as follows: The subjects were instructed to place approximately one half of the powder into a cup or beaker and to add tap water, preferably not hot water. Because lawsone is only soluble in water up to about 100 micrograms per milliliter the subjects were instructed that the powder would not completely dissolve into solution and some should be present in the bottom of the cup after mixing.

The solubility limit of lawsone in water acted as an internal control on final concentration, removing any requirement that the subjects accurately measure the amount of powder they used and ensured that similar concentration, about 100 micrograms per milliliter, was used by all subjects receiving lawsone. The subjects were further instructed to save the solution remaining after a treatment and to add additional water for the next treatment. The subjects were told not to add additional powder unless the powder dissolved completely.

The volunteers were instructed to apply the topical composition to about one half of the affected area(s) of their skin by, e.g., dabbing the composition onto the skin with a cotton ball, a cloth, paper tissue, paper towel, or the like. The remaining one half of the affected area(s) was considered a control area and was treated only with water.

The subjects were instructed to self-administer the solution as follows: On the first day the subjects were instructed to apply a freshly made solution to the affected area of their skin. A second application was to be made when the itching returned. On the second and following days two or three treatments were recommended but self-administration was unrestrained.

For comparative purposes, the subjects were asked to treat a portion of their affected areas only with water. However, if that area was very uncomfortable the subjects were asked to withhold the 1,4-naphthoquinone treatment for only the first day.

The subjects were provided with sufficient lawsone to make a topical composition for at least several days, if not weeks, of applications. The subjects treated themselves and recorded the effects of the topical composition by filling out a questionnaire. If the lawsone was used on the control area from the second day onward the subjects noted this on the questionnaire.

All subjects receiving lawsone during the trial indicated that the topical composition provided complete relief from the itching of poison ivy, induced dermatitis. The relief was reported to last from one to six hours. At this point the subjects could reapply the topical composition. No relief was demonstrable from the water applied to control areas in the trial. Additionally, about one third of the subjects reported accelerated healing of the affected areas of their skin. However, in this study controls were not in place to distinguish the effects of the topical composition from the effects of the subjects refraining from scratching affected areas.

Example 6

Clinical Evidence of Effectiveness with Additional Naphthquinones

In this example a clinical trial is conducted essentially as described above except that the 1,4-naphthoquinones selected from the lapachols, phthiocols, 2-hydroxy-juglones, 3-hydroxy-juglones, flaviolins, lawsones and other related compounds are used as the test compounds. These 1,4-naphthoquinones are obtained from commercial sources and prepared for distribution in predetermined amounts to be used in topical compositions of predetermined final concentrations. The final concentrations should be well below the amounts that can be sensitizing or irritating in humans. (see e.g. Lepoittevin and Benezra 1991; and Schulz et al. 1977, both incorporated above). Simple pretesting of skin can be required to assess irritation (e.g., allergenicity). If a compound is too irritating it is not recommended for use in the method, composition or kits described herein.

Subjects are obtained from human volunteers presenting with contact dermatitis with itching. The subjects are divided into treatment groups receiving each of the test compounds and one or more control groups receiving a placebo compound. Each subject is instructed in the conduct of the clinical trial.

The subjects are instructed in the preparation of and self-administration of topical compositions containing a test compound (or a placebo). The subjects self administer the topical composition one or more times the first day of treatment as needed and for one to three days thereafter. The volunteers record the effectiveness of the tested compounds in relieving the itching associated with the dermatitis by responding to a questionnaire.

The results of the trial are analyzed by review of the questionnaires and the effectiveness of the tested compounds in providing relief from itching is determined.

What is claimed is:

1. A method for the treatment of itching in a mammal comprising administering to the affected area a topical formulation containing an effective amount of a 1,4-naphthoquinone of the formula wherein either R or R' is a hydroxyl or a methoxy group and the other one of R or R', is selected from the group consisting of hydrogen, hydroxyl, methyl, methoxy, quaternary amine, a cycloalkyl group containing 3 to 7 carbon atoms, an alkyl, 1-alkylaminoalkyl, 1-alkenyl or alkanoyl groups of 2 to 3 carbons, and wherein the aromatic ring of said 1,4-naphthoquinone is unsubstituted or substituted with one or more groups selected from the group consisting of a halogen, phosphates, nitrates, sulphates, methoxy, carboxy, carboxylates or carboxy alkyl groups where the alkyl group comprises 2 to 3 carbons, hydroxy or hydroxylates, quaternary amines, glucosyl or glucosylamine groups, branched or straight chain alkyl groups comprising 2 to 3 carbons and methyl groups, or an effective amount of a pharmaceutically acceptable salt thereof, in a pharmaceutically acceptable carrier, to relieve the itching.

2. The method according to claim 1 wherein said 1,4-naphthoquinone is selected from the group consisting of lawsones, lapachols, phthiocols, 2-hydroxy-juglones and 3-hydroxy-juglones.

3. The method according to claim 2 wherein said 1,4-naphthoquinone is a lawsone.

4. The method according to claim 2 wherein said 1,4-naphthoquinone is present in said carrier at a concentration from at least about 20 to about 100 parts per million.

5. The method according to claim 1 wherein said mammal is a human.

6. The method according to claim 2 wherein said 1,4-naphthoquinone is present in said carrier at a concentration from about 50 to about to 100 parts per million.

7. The method according to claim 4 wherein said pharmaceutically acceptable carrier is an aqueous carrier.

8. The method of claim 1, wherein the aromatic ring of the 1,4-naphthoquinone is substituted with a halogen.

9. The method of claim 1, wherein the aromatic ring of the 1,4-naphthoquinone is substituted with a phosphate group.

10. The method of claim 1, wherein the aromatic ring of the 1,4-naphthoquinone is substituted with a nitrate group.

11. The method of claim 1, wherein the aromatic ring of the 1,4-naphthoquinone is substituted with a sulphate group.

12. The method of claim 1, wherein the aromatic ring of the 1,4-naphthoquinone is substituted with a methoxy group.

13. The method of claim 1, wherein the aromatic ring of the 1,4-naphthoquinone is substituted with a carboxy group.

14. The method of claim 1, wherein the aromatic ring of the 1,4-naphthoquinone is substituted with a carboxylate group.

15. The method of claim 1, wherein the aromatic ring of the 1,4-naphthoquinone is substituted with a carboxy group comprising 2 to 3 carbons.

16. The method of claim 1, wherein the aromatic ring of the 1,4-naphthoquinone is substituted with a hydroxy group.

17. The method of claim 1, wherein the aromatic ring of the 1,4-naphthoquinone is substituted with a hydroxylate group.

18. The method of claim 1, wherein the aromatic ring of the 1,4-naphthoquinone is substituted with a quaternary amine group.

19. The method of claim 1, wherein the aromatic ring of the 1,4-naphthoquinone is substituted with a glucosyl group.

20. The method of claim 1, wherein the aromatic ring of the 1,4-naphthoquinone is substituted with a glucosylamine group.

21. The method of claim 1, wherein the aromatic ring of the 1,4-naphthoquinone is substituted with a branched or straight chain alkyl group comprising 2–3 carbons.

22. The method of claim 1, wherein the aromatic ring of the 1,4-naphthoquinone is substituted with a methyl group.

23. A method for the treatment of itching of the skin of a mammal comprising administering to the affected area of the skin of a mammal in need of such treatment a topical formulation containing an effective amount of a compound selected from the group consisting of 5-hydroxy-1,4-naphthoquinone, 6-methyl juglone and 8-ketojuglone, in a pharmaceutically acceptable carrier, to relieve the itching.

24. The method according to claim 23 wherein said compound is 5-hydroxy-1,4 naphthoquinone.

25. The method according to claim 23 wherein said compound is present in said carrier at a concentration from at least about 20 to about 100 parts per million.

26. The method according to claim 25 wherein said pharmaceutically acceptable carrier is an aqueous carrier.

27. The method according to claim 23 wherein said mammal is a human.

28. The method according to claim 23 wherein said compound is present in said carrier at a concentration from about 50 to about to 100 parts per million.

* * * * *